United States Patent [19]

Ramsay et al.

[11] Patent Number: 5,001,145
[45] Date of Patent: Mar. 19, 1991

[54] MACROLIDE COMPOUNDS

[75] Inventors: Michael V. J. Ramsay, South Harrow; Derek N. Evans, South Ruislip; Derek R. Sutherland, Chalfont St Giles; Edward P. Tiley, Pinner; John B. Ward, Chorleywood; Neil Porter, Pinner; Hazel M. Noble, Aylesbury; Richard A. Fletton, Ruislip; David Noble, Aylesbury, all of England

[73] Assignee: American Cyanamid Company, Stamford, Conn.

[21] Appl. No.: 302,205

[22] Filed: Jan. 27, 1989

[30] Foreign Application Priority Data

Jan. 28, 1988 [GB] United Kingdom ............... 8801908

[51] Int. Cl.$^5$ ............... A61K 31/365; C07D 493/20
[52] U.S. Cl. ............................................ 514/450; 514/63; 514/409; 514/278; 514/432; 514/444; 546/14; 546/15; 548/406; 548/407; 549/28; 549/60; 549/214; 549/264
[58] Field of Search ............... 549/264, 60, 28, 214; 514/450, 432, 444, 63, 409, 514/278; 536/7.1; 546/270, 14, 15; 548/406, 407

[56] References Cited

U.S. PATENT DOCUMENTS

| Re. 32,034 | 11/1985 | Chabala et al. | 547/264 |
|---|---|---|---|
| 4,427,663 | 1/1984 | Mrozik | 536/7.1 |
| 4,916,120 | 4/1990 | Röben et al. | 549/264 |

FOREIGN PATENT DOCUMENTS 238258 9/1987 European Pat. Off. ............. 536/7.1

OTHER PUBLICATIONS

H. Mrozik et al., *J. Med. Chem.*, "Avermectin Acyl Derivatives with Anthelminticactivity," 25(6), pp. 658–663 (1982).

*Primary Examiner*—Richard L. Raymond
*Assistant Examiner*—Mark L. Russell
*Attorney, Agent, or Firm*—Carmella A. O'Gorman

[57] ABSTRACT

Compounds are described of formula (1)

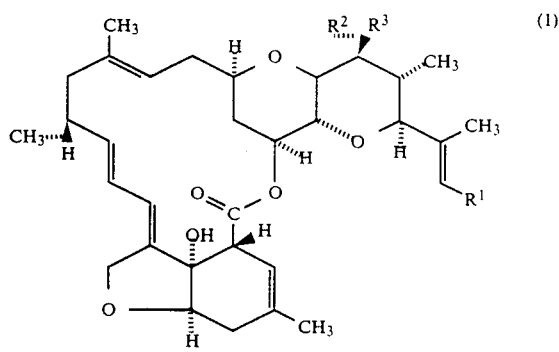

and salts thereof wherein $R^1$ is a methyl, ethyl or isopropyl group;

$R^2$ represents a hydrogen atom or a group $OR^4$ (where $OR^4$ is a hydroxyl group or a substituted hydroxyl group having up to 25 carbon atoms) and $R^3$ represents a hydrogen atom, or $R^2$ and $R^3$ together with the carbon atom to which they are attached represent $>C=CH_2$, $>C=O$ or $>C=NOR^5$ (where $R^5$ is a hydrogen atom or a $C_{1-8}$ alkyl group and the group $>C=NOR^5$ is in the E configuration).

These compounds may be used for controlling insect, acarine, nematode or other pests.

9 Claims, No Drawings

MACROLIDE COMPOUNDS

This invention relates to new antibiotic compounds and to processes for their preparation.

Thus, in one aspect, the invention provides the compounds of formula (1):

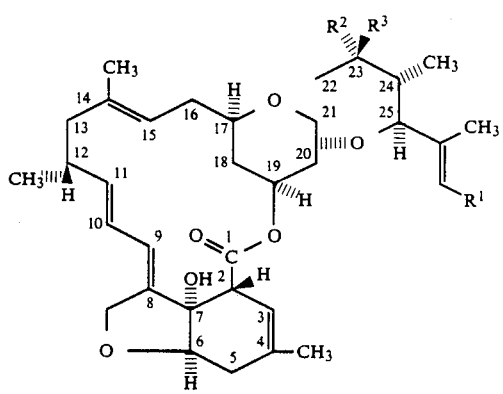

and salts thereof wherein $R^1$ is a methyl, ethyl or isopropyl group;

$R^2$ represents a hydrogen atom or a group $OR^4$ (where $OR^4$ is a hydroxyl group or a substituted hydroxyl group having up to 25 carbon atoms) and $R^3$ represents a hydrogen atom, or $R^2$ and $R^3$ together with the carbon atom to which they are attached represent $>C=CH_2$, $>C=O$ or $>C=NOR^5$ (where $R^5$ is a hydrogen atom of a $C_{1-8}$ alkyl group and the group $>C=NOR^5$ is in the E configuration).

When the compounds of formula (1) are to be used as intermediates, the group $R^2$ will often be a protected hydroxy group and the invention particularly includes such protected compounds.

Salts that may be formed with compounds of formula (1) containing an acidic group include salts with bases e.g. alkali metal salts such as sodium and potassium salts.

When the groups $R^2$ in compounds of formula (1) is a substituted hydroxyl group it may be an acyloxy group [e.g. a group of the formula $-OCOR^6$, $-OCO_2R^6$ or $-OCSOR^6$ (where $R^6$ is an aliphatic, araliphatic or aromatic group, for example an alkyl, alkenyl, alkynyl, cycloalkyl, aralkyl or aryl group)], a formyloxy group, a group $-OR^7$ [where $R^7$ is as defined above for $R^6$], a group $-OSO_2R^8$ [where $R^8$ is a $C_{1-4}$ alkyl or $C_{6-10}$ aryl group), a silyloxy group, a cyclic or acyclic acetaloxy group, a group $OCO(CH_2)_nCO_2R^9$ (where $R^9$ is a hydrogen atom or a group as defined for $R^6$ above and n represents zero, 1 or 2) or a group $R^{10}R^{11}NCO_2$ (where $R^{10}$ and $R^{11}$ may each independently represent a hydrogen atom or a $C_{1-4}$ alkyl group).

Where $R^6$ or $R^7$ are alkyl groups, they may be for example $C_{1-8}$ alkyl groups e.g. methyl, ethyl, n-propyl, i-propyl, n-butyl, i-butyl, t-butyl or n-heptyl which alkyl groups may also be substituted. Where $R^6$ is a substituted alkyl group it may be substituted by, for example, one or more, e.g. two or three halogen atoms (e.g. chlorine or bromine atoms), or a carboxy, $C_{1-4}$ alkoxy (e.g. methoxy, ethoxy), phenoxy or silyloxy group. Where $R^7$ is a substituted alkyl group it may be substituted by one or more halogen atoms (e.g. chlorine or bromine atoms, or a $C_{1-4}$ alkoxy (e.g. methoxy or ethoxy) or cycloalkyl e.g. cyclopropyl group.

Where $R^6$ or $R^7$ are alkenyl or alkynyl groups, they may be for example $C_{2-8}$ alkenyl, e.g. allyl, or $C_{2-8}$ alkynyl groups.

Where $R^6$ or $R^7$ are cycloalkyl groups, they may be for example $C_{3-12}$ cycloalkyl, such as $C_{3-7}$ cycloalkyl, e.g. cyclopentyl groups.

Where $R^6$ to $R^7$ are aralkyl groups, they preferably have 1 to 6 carbon atoms in the alkyl moiety and the aryl group(s) may be carbocyclic or heterocyclic and preferably contain 4-15 carbon atoms e.g. phenyl. Examples of such groups include phen$C_{1-6}$alkyl, e.g. benzyl groups.

Where $R^6$ or $R^7$ are aryl groups, they may be carbocyclic or heterocyclic and preferably have 4-15 carbon atoms, and may be for example a phenyl group.

When $R^2$ is a group $-OSO_2R^8$, it may be for example a methylsulphonyloxy or p-toluenesulphonyloxy group.

Where $R^2$ represents a cyclic acetaloxy group, it may for example have 5-7 ring members and may be for example a tetrahydropyranyloxy group.

When $R^2$ represents a silyloxy group or $R^6$ contains a silyloxy substituent, the silyl group may carry three groups which may be the same or different, selected from alkyl, alkenyl, alkoxy, cycloalkyl, aralkyl, aryl and aryloxy groups. Such groups may be as defined above for $R^6$ and particularly include methyl, t-butyl and phenyl groups. Particular examples of such silyloxy groups are trimethylsilyloxy and t-butyldimethylsilyloxy.

When $R^2$ represents a group $-OCO(CH_2)_nCO_2R^9$ it may for example be a group $OCOCO_2R^9$ or $OCOCH_2CH_2CO_2R^9$ where $R^9$ represents a hydrogen atom or a $C_{1-4}$ alkyl (e.g. methyl or ethyl) group.

When $R^2$ represents a group $R^{10}R^{11}NCO_2-$, $R^{10}$ and $R^{11}$ for example may each independently represent a hydrogen atom or a methyl or ethyl group.

In the compounds of formula (I) $R^5$ represents, for example, a methyl, ethyl, n-propyl, n-butyl, i-butyl or t-butyl group, and is preferably a methyl group.

An important group of compounds of formula (I) is that in which $R^1$ represents a methyl, ethyl or isopropyl group, $R^2$ represents a group $OR^4$ (where $OR^4$ is a hydroxy group or a substituted hydroxy group having up to 25 carbon atoms) and $R^3$ represents a hydrogen atom. Such compounds in which $R^2$ represents a hydroxy, acetoxy or ethoxy group are particularly preferred.

Another important group of compounds of formula (I) is that in which $R^1$ is a methyl, ethyl or isopropyl group and $R^2$ and $R^3$ together with the carbon atom to which they are attached form a group $>C=NOR^5$ (where $R^5$ is a $C_{1-8}$ alkyl group). Such compounds in which $R^5$ represents a methyl group are particularly preferred.

In the compounds of formula (I), the group $R^1$ is preferably an isopropyl group.

As indicated previously, the compounds according to the invention may be of use as antibiotics and/or as intermediates for the preparation of other active compounds. When the compounds of the invention are to be used as intermediates, the $R^2$ group may be a protected hydroxyl group. It will be appreciated that such a group should have the minimum of additional functionality to avoid further sites of reaction and should be such that it is possible to selectively regenerate a hydroxyl group from it. Examples of protected hydroxyl groups are well known and are described, for example, in "Protective Groups in Organic Synthesis" by Theodora W. Green. (Wiley-Interscience, New York 1981) and "Protective Groups in Organic Chemistry" by J F W McOmie (Plenum Press, London, 1973). Examples of $R^2$ protected hydroxy groups include phenoxyacetoxy, silyloxyacetoxy, (e.g. trimethylsilyloxyacetoxy and t-butyldimethylsilyloxyacetoxy), and silyloxy such as trimethylsilyloxy and t-butyldimethylsilyloxy. Compounds of the invention containing such groups will primarily be of use as intermediates. Other groups, such as acetoxy, may serve as protected hydroxyl groups, but may also be present in final active compounds.

Compounds of the invention have antibiotic activity e.g. antihelminthic activity, for example against nematodes, and in particular, anti-endoparasitic and anti-ectoparasitic activity.

The compounds of the invention are therefore of use in treating animals and humans with endoparasitic and/or ectoparasitic infections.

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

The compounds according to the invention have been found to be effective both in vitro and in vivo against a range of endoparasites and ectoparasites. The antibiotic activity of compounds of the invention may, for example, be demonstrated by their activity against free living nematodes e.g. *Caenorhabiditis elegans.* In particular, we have found that compounds of the invention are active against parasitic nematodes such as *Nematospiroides dubius.*

Compounds of the invention are also of use as antifungals, for example, against strains of Candida sp. such as *Candida albicans* and *Candida glabrata* and against yeast such as *Saccharomyces carlsbergensis.*

Compounds of the invention are also of use in combating insect, acarine and nematode pests in agriculture, horticulture, forestry, public health and stored products. Pests of soil and plant crops, including cereals (e.g. wheat, barley, maize and rice), cotton, tobacco, vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius;* flour beetles such as *Tribolium castaneum;* flies such as *Musca domestica;* fire ants; leaf miners; *Pear psylla; Thrips tabaci;* cockroaches such as *Blatella germanica* and *Periplaneta americana* and mosquitoes such as *Aedes aegypti.*

According to the invention we therefore provide compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or vegetation) or a locus thereof or to the pests themselves.

Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds according to the invention may be formulated for use in veterinary or human medicine by injection and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil or cottonseed oil, mineral oils such as liquid paraffin, and ethyl oleate and other similar compounds. Other vehicles such as propylene glycol may also be used.

Compositions for verterinary medicine may also be formulated as intramammary preparations in either long acting or quick-release bases and may be sterile solutions or suspensions in aqueous or oily vehicles optionally containing a thickening or suspending agent such as soft or hard paraffins, beeswax, 12-hydroxy stearin, hydrogenated castor oil, aluminium stearates, or glyceryl monostearate. Conventional non-ionic, cationic, or anionic surface active agents may be used alone or in combination in the composition.

The compounds of the invention may also be presented for veterinary or human use in a form suitable for oral administration, for example in the form of solutions, syrups or suspensions, or a dry powder for constitution with water or other suitable vehicle before use, optionally with flavouring and colouring agents. Solid compositions such as tablets, capsules, lozenges, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form. Examples of suitable pharmaceutically acceptable carriers for use in solid dosage forms include binding agents (e.g. pregelatinised maize starch, polyvinylpyrrolidone or hydroxypropyl methylcellulose); fillers (e.g. lactose, micro-crystalline cellulose or calcium phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art.

Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid); stabilising and solubilising agents may also be includeed.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates, non-aqueous vehicles e.g. arachis oil or oily esters; stabilising and solubilising agents. The compounds of the invention may also be administered in veterinary medicine by incorporation thereof into animals daily solid or liquid dietary intake, e.g. as part of the daily animal feed or drinking water.

The compounds of the invention may also be administered orally in veterinary medicine in the form of a liquid drench such as a solution, suspension or dispersion of the active ingredient together with a pharmaceutically aceptable carrier or excipient.

The compounds of the invention may also, for example, be formulated as suppositories e.g. containing conventional suppository bases for use in veterinary or human medicine or as pessaries e.g. containing conventional pessary bases.

Compounds according to the invention may be formulated for topical administration, for use in veterinary and human medicine, as ointments, creams, lotions, shampoos, powders, pessaries, sprays, dips, aerosols, drops (e.g. eye or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents e.g. stabilising and solubilising agents.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Drops may be formulated with an aqueous or non aqueous base also comprising one or more dispersing agents, stabilising agents, solubilising agents or suspending agents. They may also contain a preservative.

For topical administration by inhalation the compounds according to the invention may be delivered for use in veterinary or human medicine in the form of an aerosol spray presentation or an insufflator.

The compounds of the invention may be administered in combination with other pharmaceutically active ingredients.

The total daily dosages of compounds of the invention employed in both veterinary and human medicine will suitably be in the range 1–2000μg/kg bodyweight, preferably from 50–1000μg/kg and these may be given in dividend doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by contentional methods such as, for example by blending and/or grinding of the active ingredient(s) together with the carrier or diluent, e.g. solid carrier, solvent or surface active agent.

Suitable solid carriers, for use in the formulations such as dusts, granulates and powders may be selected from for example natural mineral fillers, such as diatomite, talc, kaolinite, montmorillonite prophyllite or attapulgite. Highly dispersed silicic acid or highly dispersed absorbent polymers may, if desired, be included in the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, esters, ketones, acid amides, strongly polar solvents, optionally epoxidized vegetable oils and water.

Conventional non-ionic, cationic or anionic surface-active agents, e.g. ethoxylated alkyl phenols and alcohols, alkali metal or alkaline earth metal salts of alkyl benzene sulphonic acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-foaming agents, viscosity regulators, binders and adhesives, photostabilisers as well as fertilizers, feeding stimulants or other active substances may, if desired, be included in the compositions. The compounds of the invention may also be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The compounds of the invention may be prepared by the processes discussed below. In the following formulae, $R^1$, $R^2$ and $R^3$ are as defined in formula (1) unless otherwise stated.

Thus, according to a further aspect of the invention we provide a process (A) for the preparation of compounds of formula (1) which comprises reducing a compound of formula (2)

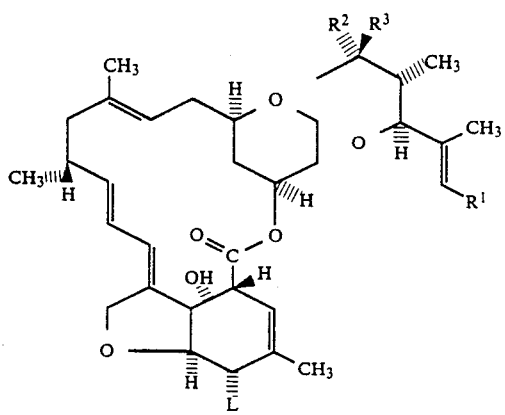

[wherein L represents an atom or group removable by reduction, for example, by homolytic reduction, such as a halogen atom (eg a chlorine, bromine or iodine atom), a group $R^{12}OC(=S)O-$ (where $R^{12}$ is $C_{1-6}$ alkyl, aryl such as phenyl, or ($C_{1-6}$ alkyl) aryl such as p-tolyl) or a group $R^{13}O_2CC(=O)O-$ (where $R^{13}$ is $C_{1-4}$ alkyl e.g. methyl or ethyl)].

The reduction may be effected using a reducing agent such as an alkyl tin hydride (eg tri-n-butyl tin hydride) in the presence of a radical initiator such as a peroxide, azobisisobutyronitrile or light.

The reaction may conveniently be effected in a suitable solvent such as a hydrocarbon, eg hexane, benzene or toluene. Combinations of such solvents may also be used.

The reaction may be carried out at a temperature of from 0° to 200° C., preferably from 20° to 130° C.

When L in the compounds of formula (2) represents a halogen atom the compounds have the precise structure (2a)

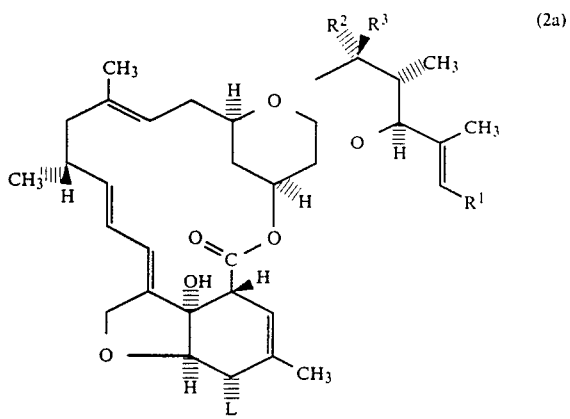

and when L in the compounds of formula (2) represents a group $R^{12}OC(=S)O-$ or $R^{13}O_2CC(=O)O-$ the compounds have the precise structure (2b)

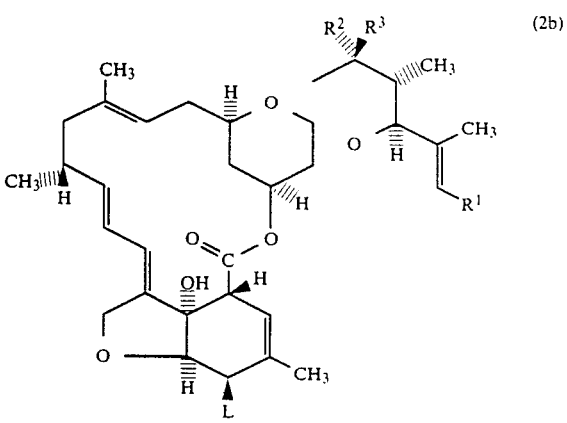

The intermediates of formula (2a) are novel compounds and form a further aspect of the invention.

It will be appreciated that certain compounds of formula (1) in which $R^2$ is a substituted hydroxyl group cannot be prepared according to Process (A). We therefore provide herewith a further process (B) which comprises preparing compounds of formula (1) in which $R^2$ is a substituted hydroxyl group from the corresponding compounds of formula (1) in which $R^2$ is a hydroxyl group by reaction with reagents serving to form a substituted hydroxyl group. The reaction will in general be an acylation, formylation, sulphonylation, etherification, silylation or acetal formation.

Thus, for example, acylation may be effected using an acylating agent such as an acid of formula $R^6COOH$ or a reactive derivative thereof, such as an acid halide (e.g. acid chloride), anhydride or activated ester, or a reactive derivative of a carbonic acid $R^6OCOOH$ or thiocarbonic acid $R^6OCSOH$.

Acylations employing acid halides and anhydrides may if desired be effected in the presence of an acid binding agent such as a tertiary amine (e.g. triethylamine, diemthylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acylations employing acids are desirably conducted in the presence of a condensing agent, for example a carbodiimide such as N,N'-dicyclohexylcarbodiimide or N-ethyl-N'γ-dimethylaminopropylcarbodiimide; a carbonyl compound such as carbonyldiimidazole; or an isoxazolium salt such as N-ethyl-5-phenylisoxazolium perchlorate.

An activated ester may conveniently be formed in situ using, for example, 1-hydroxybenzotriazole in the presence of a condensing agent as set out above. Alternatively, the activated ester may be preformed.

The acylation reaction may be effected in non-aqueous reaction media, conveniently at a temperature in the range $-20°$ to $+100°$ C., e.g. $-10°$ to $+50°$ C.

Formylation may be effected using an activated derivative of formic acid e.g. N-formyl imidazole or formic acetic anhydride under standard reaction conditions.

Sulphonylation may be effected with a reactive derivative of a sulphonic acid $R^8 SO_3H$ such as a sulphonyl halide, for example a chloride $R^8SO_2Cl$. The sulphonylation is preferably effected in the presence of a suitable acid binding agent as described above.

Etherification may be effected using a reagent of formula $R^7Y$ (where $R^7$ is as previously defined and Y represents a leaving group such as chlorine, bromine or iodine atom or a hydrocarbylsulphonyloxy group, such as mesyloxy or tosyloxy, or a haloalkanoyloxy group such as dichloroacetoxy). The reaction may be carried out by formation of a magnesium alkoxide using a Grignard reagent such as a methylmagnesium halide e.g. methylmagnesium iodide or using a trialkylsilylmethylmagnesium halide e.g. trimethylsilylmethylmagnesium chloride followed by treatment with the reagent $R^7Y$.

Alternatively, the reaction may be effected in the presence of a silver salt such as silver oxide, silver perchlorate, silver carbonate or silver salicylate or mixtures thereof, and this system may be particularly appropriate when etherification is carried out using an alkyl halide (e.g. methyl iodide).

Etherification may conveniently be effected in a solvent such as an ether e.g. diethyl ether.

Acetal formation may be carried out by reaction with a cyclic or acyclic vinyl ether. This method is especially useful for production of tetrahydropyranyl ethers, using dihydropyran as reagent, or 1-alkoxyalkyl ethers such as 1-ethoxyalkyl ether, using an alkyl vinyl ether as reagent. The reaction is desirably carried out in the presence of a strong acid catalyst, for example a mineral acid such as sulphuric acid, or an organic sulphonic acid such as p-toluene sulphonic acid, in a non-hydroxylic, substantially water-free solvent.

Silylation may be effected by reaction with a silyl halide (e.g. chloride), advantageously in the presence of a base such as imidazole, triethylamine or pyridine, using a solvent such as dimethylformamide.

The compounds of formula (2) may be prepared from the corresponding 5-hydroxy compounds of formula (3)

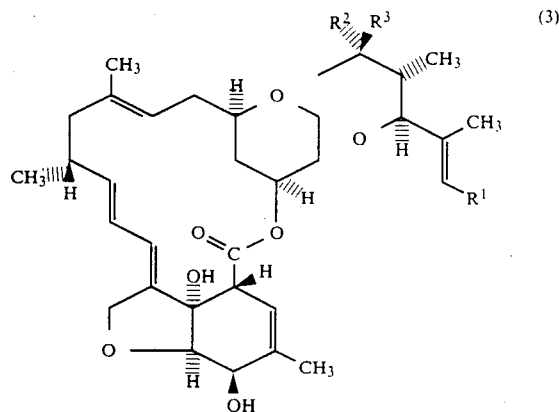

Thus, the compounds of formula (2a) may be prepared by treating a compound of formula (3) with a suitable halogenating agent. For example, chlorination may be achieved by treatment with a reagent $(R^{14}O)_2P(=O)Cl$ (where $R^{14}$ is an halogenated alkyl group eg $CCl_3CH_2—$) in the presence of a trialkylamine (eg diisopropylethylamine) and dimethylaminopyridine. Alternatively, chlorination may be effected using a triarylphosphine (eg triphenylphosphine) and carbon tetrachloride in a solvent such as a nitrile (eg acetonitrile).

Compounds of formula (2b) in which L represents $R^{12}OC(=S)O—$ may be prepared by treating a compound of formula (3) with a reagent $R^{12}OC(=S)Cl$ in a suitable solvent, eg a halogenated hydrocarbon such as dichloromethane at low temperature eg 0° C.

Compounds of formula (2b) in which L represents $R^{13}O_2CC(=O)O—$ may be prepared by treating a compound of formula (3) with a reagent $R^{13}O_2CC(=O)Cl$ in the presence of an alkali metal carbonate such as calcium carbonate and in a solvent such as a ether eg diethyl ether.

Compounds of formula (3) in which $R^2$ is a hydrogen atom or a group $OR^4$ and $R^3$ is a hydrogen atom, or $R^2$ and $R^3$ together with the carbon atom to which they are attached represent $>C=O$ are described in UK Patent Specification no 2176182A.

Compounds of formula (3) in which $R^2$ and $R^3$ together with the carbon atom to which they are attached represent $>C=CH_2$ may be prepared by reacting the corresponding known 23-keto compounds (i.e. compounds of formula (3) in which $R^2$ and $R^3$ together with the carbon atom to which they are attached represent $>C=O$) with an appropriate Wittig reagent e.g. a phosphorane of formula $(R^a)_3P=CH_2$ (where $R^a$) represents $C_{1-6}$ alkyl or aryl, e.g. monocyclic aryl such as phenyl). Suitable reaction solvents include ethers such as tetrahydrofuran or diethyl ether or a dipolar aprotic solvent such as dimethyl sulphoxide. The reaction may be carried out at any suitable temperature e.g. at 0° C.

Compounds of formula (3) in which $R^2$ and $R^3$ together with the carbon atom to which they are attached represent $>C=NOR^5$ [where $R^5$ is as defined in formula (1)] may be prepared from the corresponding 23-keto compounds by reaction with a reagent $H_2NOR^5$ (where $R^5$ is as just defined).

The reaction may conveniently be effected at a temperature in the range $-20$ to $+100°$ C., e.g. $-10$ to $+50°$ C. It is convenient to use the reagent $H_2NOR^5$ in the form of a salt, for example an acid addition salt such as the hydrochloride. When such a salt is employed the reaction may be carried out in the presence of an acid binding agent.

Solvents which may be employed include alcohols (e.g. methanol or ethanol), amides (e.g. N,N-dimethylformamide, N,N-dimethylacetamide or hexamethylphophoramide), ethers (e.g. cyclic ethers such as tetrahydrofuran or dioxan, and acylic ethers such as dimethoxyethane or diethyl ether), nitriles (e.g. acetonitrile), sulphones (e.g. sulpholane) and hydrocarbons such as halogenated hydrocarbons (e.g. methylene chloride), as well as mixtures of two or more such solvents. Water may also be employed as a cosolvent.

When aqueous conditions are employed the reaction may conveniently be buffered with an appropriate acid, base or buffer.

Suitable acids include mineral acids, such as hydrochloric or sulphuric acid, and carboxylic acid such as acetic acid. Suitable bases include alkali metal arbonates and bicarbonates such as sodium bicarbonate, hydroxides such as sodium hydroxide, and alkali metal carboxylates such as sodium acetate. A suitable buffer is sodium acetate/acetic acid.

The invention is further illustrated by the following Intermediates and Examples in which the compounds are named as derivatives of 'Factor A'. Factor A is a compound of formula (3) in which $R^1$ is isopropyl, $R^2$ is a hydroxy group and $R^3$ is hydrogen.

All temperatures are in 0° C.

INTERMEDIATE 1

(a) 5-Acetoxy-23[E]-methoxyimino Factor A

A solution of anhydrous sodium acetate (2.8 g) in water (15 ml) was added to a solution of 5-acetoxy-23-keto Factor A (3.13 g, Example 18 in UK 2176182A) in methanol, followed by methoxyamine hydrochloride (3.01 g). The resultant solution was stirred for 1.5 h at 20°, diluted with ethyl acetate then washed successively with 0.5 N hydrochloric acid, water and brine. The dried organic phase was evaporated to near dryness and the off-white foam was purified by chromatography over Merck Kieselgel 60 230-400 mesh (600 ml). Elution of the column with hexane: ethyl acetate (4:1) afforded the title compound as a colourless foam (2.14 g) $[\alpha]_D^{21} + 128°$ (C 1.35, CHCl$_3$) $\lambda_{max}$ (EtOH) 244 nm ($\epsilon_{max}$ 27,250); $\nu_{max}$ (CHBr$_3$) 3560, 3480 (OH), 1733 (acetate), 1715 (C=O), 995 (C-O), $\delta$(CDCl$_3$) include 5.5-5.6 (m:2H), 3.84 (S:3H) 3.29 (d 15;H), 2.16 (S:3H).

(b) 23[E]-Methoxyimino Factor A

A solution of the product of Intermediate 1(a) (1.88 g) in methanol was cooled in an ice bath, 1N aqueous sodium hydroxide (5.6 ml) was added, and the solution was stirred in an ice bath for 1.5 h. The solution was diluted with ethyl acetate and washed successively with 0.5N aqueous hydrochloric acid, water and brine. The dried organic phase was evaporated and the resultant foam was purified by chromatography over Merck Kieselgel 60 230-400 mesh (400 ml). Elution of the column with hexane: ethyl acetate (2:1) afforded a colourless foam (1.429 g)

Crystallisation from hexane afforded the pure title compound, m.p. 203°, $[\alpha]_D^{21} + 132°$ (c 1.21, CHCl$_3$), $=_{max}$ (EtOH) 244 nm ($\epsilon_{max}$ 29200), $\nu_{max}$ (CHBr$_3$) 3540 (OH), 1708 (C=O), 992 (C-O), $\delta$(CDCl$_3$) includes 4.29 (t7:1H), 3.84 (s:3H), 3.29 (d15:1H).

INTERMEDIATE 2

5-epi-Chloro, 23-[E]-Methoximino Factor A

A solution of Intermediate 1(b) (150 mg) in dry acetonitrile (2 ml) and carbon tetrachloride (0.15 ml) was treated under nitrogen with triphenylphosphine (82 mg). After 1 hr the solution was poured into ethyl acetate (50 ml) and the organic phase then washed with water and brine. The dried organic phase was evaporated to leave a gum (189 mg) which was dissolved in dichloromethane (1 ml) and applied to a column of Merck Kieselgel 60, 230-400 mesh silica (16 g) made up in hexane:ethyl acetate (4:1). Elution of the column under pressure with the same solvent system afforded the title compound as a foam (96 mg), $\lambda_{max}^{EtOH}$ 245 ($\epsilon_{max}$ 27,500), $\nu_{max}$ (CHBr$_3$) 3500 (OH) and 1718 cm$^{-1}$ (lactone), $\delta$(CDCl$_3$) includes 0.91 (d, 6Ha; 3H), 0.96 (d, 6Hz; 3H) 1.00 (d, 6Hz; 3H), 1.04 (d, 6Hz; 3H), 1.94 (S; 3H), 1.94 (S; 3H), 3.12 (m; 1H), 3.29 (d, 14 Hz; 1H), 3.83 (S; 3H), 4.17 (S; 1H), 4,40 (S; 1H) and 5.56 (S; 1H).

INTERMEDIATE 3

5-epi-Chloro Factor A (a) Factor A (3.0 g ) in dry acetonitrile (35 ml) under nitrogen was treated with carbon tetrachloride (4.7 ml) and triphenylphosphine (2.57 g). After 1 1/4 hr. chromatographic purification of the resulting crude mixture according to the procedure in Intermediate 2 afforded the title compound (1.34 g) as a yellow foam $[\alpha]_D^{21} + 145$ (c 0.5, CHCl$_3$) 239 ($\epsilon$ 35,500) and 245.5 nm ($\epsilon$max 36,500), vmax (CHBr$_3$) 3500 (OH) and 1720 cm$^{-1}$(lactone, $\delta$ (CDCl$_3$) includes 0.79 (d, 6Hz; 3H), 0.96 (d, 6Hz; 3H) 1.00 (d, 6Hz; 3H), 1.05 (d, 6Hz; 3H), 1.05 (d, 6Hz; 3H), 1.95 (s; 3H) 3.12 (m; 1H), 3.52 (s; 1H), 3.79 (dq; 11 and 2Hz; 1H), 4.16 (s; 1H), 4.40 (s; 1H) and 5.55 (s; 1H).

(b) Factor A (1.2 g) in dry tetrahydrofuran (10 ml) was treated under nitrogen with 2,2,2-trichloroethyl phosphorochloridate (3.2 g) int he presence of N,N-diisopropylethylamine (3.41 ml), and 4-dimethylaminopyridine (347 mg). After 3½ hr the resulting mixture was diluted with ether (100 ml) and the organic solution then washed sequentially with N hydrochloric acid, saturated bicarbonate, water and brine. Drying and evaporation of the organic phase gave a gum (3.74 g) which was purified by chromatography over Merck Kieselgel 60 (300 g) eluting the column with hexane: ethyl acetate (4:1) and (3:1) to give the title compound (554 mg). The nmr spectrum was similar to that of the sample prepared according to the procedure described in (a) above.

INTERMEDIATE 4

5-epi-Chloro,23-Keto Factor A

23-Keto Factor A (646 mg, Example 21 in UK 2176182A) in dry tetrahydrofuran (5 ml), under nitrogen, was treated with N,N-diisopropylethylamine (1.84 ml) and 4-dimethylaminopyridine (375 mg) followed by 2,2,2-trichloroethyl phosphorochloridate (4.01 g). After 1 1/4 hr the mixture was worked up and purified according to the procedure of Intermediate 3(b) above to give the title compound as a foam (446 mg), $[\alpha]_D^{21} + 154°$ (S 0.9, CHCl$_3$), $\lambda_{max}^{EtOH}$ 246 nm ($\epsilon$max 23,000) $\nu$max (CHBr$_3$) 3550 and 3480 (OH), and 1716 cm$^{-1}$ (CO$_2$R), $\delta$ (CDCl$_3$) includes 0.81 (d, 6Hz; 3H), 0.97 (d, 6Hz; 3H), 1.02 (d, 6Hz; 3H), 1.52 (s; 3H), 1.71 (s;

3H), 1.96 (s; 3H), 3.14 (m; 1H), 3.48 (s; 1H), 3.71 (d, 10Hz; 1H), 4.17 (s; 1H), 4.40 (s; 1H) and 2.48 (s; 2H).

INTERMEDIATE 5

5-epi-Chloro, 23-desoxy Factor A 2,2,2-Trichloroethyl phosphrochloridate (2.67 g) was added, under nitrogen, to a stirred solution of 23-desoxy Factor A (978 mg, Example 27 in UK 2176182A), N,N-diisopropylethylamine (2.85 ml) and 4-dimethylaminopyridine (290 mg) in dry tetrahydrofuran (16 ml). After 1½ hr the mixture was worked up and purified according to the procedure of Intermediate 3(b) above to give the title compound (514 mg), $\lambda_{max}^{EtOH}$ 244.6 nm ($\epsilon$max 18,200), $\delta$ (CDCl$_3$) includes 0.68 (d, 5Hz; 3H), 0.94 (d, 6Hz; 3H), 1.01 (d, 6Hz; 3H), 1.05 (d, 6Hz; 3H), 1.52 (s; 3H), 1.59 (s; 3H), 1.95 (s; 3H), 3.12 (m; 1H), 3.42 (d, 9Hz; 1H), 3.66 (s; 3H), 4.17 (s; 1H) and 4.40 (s; 1H).

INTERMEDIATE 6

5-Methyl oxalate, 23-desoxy Factor A

A mixture of 23-desoxy Factor A (120 mg), calcium carbonate (60 mg) and methyl oxalyl chloride (108 mg) was stirred for 59 hr before being partitioned between 2N hydrochloric acid:ether (1:1, 40 ml). The organic phase was separated, washed with water and brine and was then dried and evaporated to a foam (110 mg) which was purified by flash chromatography over Kieselgel 60, 230–400 mesh silica (25 g). Elution of the column with hexane:ethyl acetate (5:1), afforded the title compound (24 mg), $\nu$max (CHBr$_3$) 3470 (OH), 1770 and 1740 (OCOCO $_2$Me) and 1708 cm$^{-1}$ (CO$_2$R), $\delta$ (CDCl$_3$) includes 0.69 (d, 5Hz; 3H), 0.94 (d, 6Hz; 3H), 0.99 (d, 6Hz; 3H), 1.03 (d, 6Hz; 3H), 1.81 (s; 3H), 3.38 (m; 1H), 3.42 (d, 10Hz; 1H), 3.91 (s; 3H) and 5.60 (m; 2H).

INTERMEDIATE 7

5-p-Tolylthionocarbonate, 23-acetoxy Factor A

To a cold solution (0° to 5° C.) of 23-acetoxy Factor A (200 mg, Example 11 in UK 2176182A) in dry dichloromethane (25 ml) was added, under nitrogen, pyridine (0.3 ml) followed by p-tolylthionochloroformate (0.1 ml). After 4 hr the reaction was partitioned between dichloromethane:2N hydrochloric acid. The organic phase was separated and washed sequentially with 2N hydrochloric acid, saturated aqueous bicarbonate and brine. The dried organic phase was evaporated and the residue purified by chromatography over Kieselgel 60 (75 g), using hexane:ethylacetate (3:1) as eluent. Appropriate fractions were combined to give the title compound (120 mg), $\lambda_{max}^{CHCl_3}$ 246.5 nm ($\epsilon$max 32,700), $\nu$max (CHBr$_3$) 3550, 3460 (OH), 1720 (CO$_2$R) and 828 cm$^{-1}$ (Tolyl), $\delta$ (CDCl$_3$) includes 0.71 (d, 6Hz; 3H), 0.96 (d, 6Hz; 3H), 1.00 (d, 6Hz; 3H), 1.86 (s; 3H), 2.03 (s; 3H), 2.37 (s; 3H), 3.40 (m; 1H), 3.91 (d, 10Hz; 1H), 4.28 (d, 5Hz; 1H), 4.90 (m; 1H), 6.09 (d, 5Hz; 1H), 7.02 (d, 8Hz; 2H) and 7.20 (d, 8Hz; 2H).

EXAMPLE 1

5-Desoxy, 23-Methoximino Factor A

A solution of Intermediate 2 (87 mg) and 2,2'-3-bis(2-methylproprionitrile) (3 mg) in refluxing dry toluene (3 ml) was treated, under nitrogen, with tri-n-butyl tin hydride (192 mg). After 15 min the solution was cooled and evaporated to leave an oil, which as a solution in hexane:ethyl acetate (4:1) was filtered through a pad of Kieselgel 60. Evaporation of the filtrate followed by preparative HLPC purification of the foam so obtained, afforded the title compound (10 mg), $[\alpha]_D^{21}$+14120 (CO.3, CHCl$_3$), $\lambda_{max}^{EtOH}$ 245 nm ($\epsilon$max 28,000), $\nu$max (CHBr$_3$) 3480 (OH) and 1700 cm$^{-1}$ (CO$_2$R), $\delta$ (CDCl$_3$) includes 0.92 (d, 6Hz; 3H), 0.96 (d, 6Hz; 3H), 0.99 (d, 6Hz; 3H), 1.05 (d, 6Hz; 3H), 1.76 (s; 3H), 3.11 (m; 1H), 3.29 (d, 14Hz; 1H), 1.92 (d, 14Hz; 1H), 3.84 (s; 3H) and 3.81 (d, 6Hz; 1H).

EXAMPLE 2

5-Desoxy Factor A

Intermediate 3 (255 mg) in benzene (5 ml) was added to a solution of tri-n-butyl tin hydride (0.54 ml) and 2,2'-3-bis (2-methylpropionitrile) (5mg), at reflux temperature. After 15 min the product was worked up and purified according to the method of Example 1 above to give the title compound (43 mg) as a white foam. $\delta$ (CDCl$_3$) includes 0.81 (d, 6Hz; 3H), 0.95 (d, 6Hz; 3H), 1.00 (d, 6Hz; 3H), 1.06 (d, 6Hz; 3H), 1.76 (s; 3H), 3.09 (m; 1H) and 5.2–5.5 (m; 3H).

EXAMPLE 3

5-Desoxy, 23-Acetoxy Factor A

A refluxing solution of Intermediate 7 (250 mg) and 2,2'-3-bis (2-methylpropionitrile) (50 mg) in toluene (30 ml) was treated with tri-n-butyl tin hydride (0.75 ml) in toluene (25 ml), added in 2 portions. After 7 hr, the product was worked up and purified according to the method of Example 1 above to give the title compound (30 mg), $\nu$max (CHBr$_3$) 3500 (OH) and 1720 cm$^{-1}$ (CO$_2$R), $\delta$ (CDCl$_3$) includes 0.69 (d, 6Hz; 3H), 1.74 (s; 3H), 2.03 (s; 3H), 3.08 (m; 1H), 3.79 (m; 2H), 4.90 (m; 1H) and 5.33 (m; 2H).

EXAMPLE 4

5-Desoxy, 23-keto Factor A

Intermediate 4 (157 mg) in benzene (2 ml) was treated with a refluxing solution of tri-n-butyl tin hydride (0.3 ml) and 2,2'-3-bis (2-methylpropio-nitrile) (4 mg) in benzene (5 ml) over 45 min. The product was worked up and purified according to the method of Example 1 above to give the title compound (25 mg) as a white foam. $[\alpha]_D^{21}$+128° (C.0.2, CHCl$_3$), $\lambda_{max}^{EtOH}$ 244.6 nm ($\epsilon$max 24,100), $\nu$max (CHBr$_3$) 3500 (OH) and 1712 cm$^{-1}$ (lactone + ketone), $\delta$(CDCl$_3$) 0.86 (d, 6Hz; 3H), 0.96 (d, 6Hz; 3H, 0.99 (d, 6Hz; 3H), 1.06 (d, 6Hz; 3H), 1.76 (s; 3H), 2.51 (s; 2H), 3.09 (m; 1H) and 3.80 (d, 5Hz; 1H).

EXAMPLE 5

5,23-Bis desoxy Factor A (a) Intermediate 5 (208 mg) in benzene (5 ml) was added to a refluxing solution of tri-n-butyl tin hydride (0.45 ml) in toluene, in the presence of 2,2'-3-(2-methylpropionitrile) (5 mg). After 15 min, at reflux temperature, the product was worked up and purified according to the method of Example 1 above to give title compound (15 mg) as a white foam, $[\alpha]_D^{21}$+172° (c 0.3, CH$_2$Cl$_2$), $\lambda_{max}^{EtOH}$236.4 ($\epsilon$max 25.800) and 245 nm ($\epsilon$max 29,500), $\nu$max (CHBr$_3$) 3500 (OH) and 1702cm$^{-1}$ (lactone), $\delta$ (CDCl$_3$) includes 0.68 (d,5Hz; 3H), 0.94 (d, 6Hz; 3H), 0.99 (d, 6Hz; 3H), 1.04 (d, 6Hz; 3H), 1.76 (s; 3H), 3.08 (m; 1H), 3.42 (d, 10Hz; 1H) and 3.81 (d, 6Hz; 1H).

(b) A refluxing solution of Intermediate 6 (13 mg) and 2,2'-3-bix(2-methylpropionitrile) (1 mg) in toluene (2 ml) was treated under nitrogen, with tri-n-butyl tin hydride (25 mg). After 1 hr the in Example 1 above to give the title compound (Yield, 18%). The product was chromatographically similar to the compound prepared in part (a) above.

EXAMPLE 6

5-Desoxy, 23-Ethoxy Factor A

5-Desoxy Factor A (61 mg), silver carbonate (474 mg), ethyl iodide (0.16 ml) and silver perchlorate (356 mg) in dry ether (8 ml) was stirred at ambient temperature for 16 hr. The mixture was filtered through a pad of Kieselghur, and the combined filtrate and washings stirred with collidine (1.5 ml) and methanol (1 ml). After 1 hr the solution was washed with water, 2N HCl and brine. The dried organic phase was evaporated to leave a foam which was purified by preparative HPLC to give the title compound (18 mg) as a white foam, $[\alpha]_D^{21}+182°$ (c 0.5, CHCl$_3$), $\lambda_{max}^{EtOH}$244.8 nm ($\epsilon$max, 28,000), $\nu$max (CHBr$_3$) 3490 (OH) and 1704 cm$^{-1}$ (lactone), $\delta$ (CDCl$_3$) includes 0.76 (d, 6Hz; 3H), 0.94 (d, 6Hz; 3H), 0.99 (d, 6Hz; 3H), 1.04 (d, 6Hz; 3H), 1.14 (t, 7Hz; 3H), 1.75 (s; 3H), 3.08 (m; 1H), 3.26 (m; 1H), 3.64 (m; 1H), 3.47 (q, 3Hz; 1H) and 5.2-5.5 (m; 3H).

The following are examples of formulations according to the invention. The term 'Active Ingredient' as used hereinafter means a compound of the invention.

MULTIDOSE PARENTERAL INJECTION

EXAMPLE 1

|  | % w/v | Range |
|---|---|---|
| Active ingredient | 2.0 | 0.1-6.0% w/v |
| Benzyl alcohol | 1.0 |  |
| Polysorbate 80 | 10.0 |  |
| Glycerol formal | 50.0 |  |
| Water for Injections | to 100.0 |  |

Dissolve the active ingredient in the polysorbate 80 and glycerol formal. Add the benzyl alcohol and make up to volume with Water for Injections. Sterilize the product by conventional methods, for example sterile filtration or by heating in an autoclave and package aseptically.

EXAMPLE 2

|  | % w/v | Range |
|---|---|---|
| Active ingredient | 4.0 | 0.1-7.5% w/v |
| Benzyl alcohol | 2.0 |  |
| Glyceryl triacetate | 30.0 |  |
| Propylene glycol | to 100.0 |  |

Dissolve the active ingredient in the benzyl alcohol and glyceryl triacetate. Add the propylene glycol and make up to volume. Sterilize the product by conventional pharmaceutical methods, for example sterile filtration, and package aseptically.

EXAMPLE 3

|  | % | Range |
|---|---|---|
| Active ingredient | 2.0 w/v | 0.1-7.5% w/v |
| Ethanol | 36.0 v/v |  |
| Non-ionic surfactant | 10.0 w/v |  |
| (e.g. Synperonic PE L44*) | 10.0 w/v |  |
| Propylene glycol | to 100.0 |  |

*Trademark of ICI

Dissolve the active ingredient in the ethanol and surfactant and make up to volume. Sterilize the product by conventional pharmaceutical methods, for example sterile filtration, and package aseptically.

EXAMPLE 4

|  | % | Range |
|---|---|---|
| Active Ingredient | 2.0 w/v | 0.1-3.0% w/v |
| Non-ionic surfactant |  |  |
| (e.g. Synperonic PE F68*) | 2.0 w/v |  |
| Benzyl alcohol | 1.0 w/v |  |
| Miglyol 840** | 16.0 v/v |  |
| Water for Injections | to 100.0 |  |

*Trademark of ICI
**Trademark of Dynamit Nobel

Dissolve the active ingredient in the Miglyol 840. Dissolve the non-ionic surfactant and benzyl alcohol in most of the water. Prepare the emulsion by adding the oily solution to the aqueous solution while homogenising using conventional means. Make up to volume. Aseptically prepare and package aseptically.

| Aerosol spray | | |
|---|---|---|
|  | % w/w | Range |
| Active Ingredient | 0.1 | 0.01-2.0% w/w |
| Trichloroethane | 29.9 |  |
| Trichlorofluoromethane | 35.0 |  |
| Dichlorodifluoromethane | 35.0 |  |

Mix the Active Ingredient with trichloroethane and fill into the aerosol container. Purge the headspace with the gaseous propellant and crimp the valve into position. Fill the required weight of liquid propellant under pressure through the valve. Fit with actuators and dust-caps.

| Tablet Method of manufacture - wet granulation | |
|---|---|
|  | mg |
| Active Ingredient | 250.0 |
| Magnesium stearate | 4.5 |
| Maize starch | 22.5 |
| Sodium starch glycolate | 9.0 |
| Sodium lauryl sulphate | 4.5 |
| Microcrystalline cellulose | to tablet core weight of 450 mg |

Add sufficient quantity of a 10% starch paste to the active ingredient to produce a suitable wet mass for ganulation. Prepare the granules and dry using a tray or fluid-bed drier. Sift through a sieve, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

| Veterinary tablet for small/domestic animal use Method of manufacture - dry granulation | |
| --- | --- |
| | mg |
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

| Veterinary intrammary injection | | | |
| --- | --- | --- | --- |
| | | mg/dose | Range |
| Active Ingredient | | 150 mg | 0.05–1.0 g |
| Polysorbate 60 | 3.0% w/w | | |
| White Beeswax | 6.0% w/w | to 3 g | to 3 or 15 g |
| Arachis oil | 91.0% w/w | | |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringe.

| Veterinary slow-release bolus | | |
| --- | --- | --- |
| | % w/w | Range |
| Active Ingredient | | 0.25–2 g |
| Colloidal silicon dioxide | 2.0 | to required fill weight |
| Microcrystalline cellulose | to 100.0 | |

Blend the active ingredient with the colloidal silicon dioxide and microcrystalline cellulose by using a suitable aliquot blending technique to achieve a satisfactory distribution of active ingredient throughout the carrier. Incorporate into the slow release device and give (1) a constant release of active ingredient or (2) a pulsed release of active ingredient

| Veterinary oral drench | | |
| --- | --- | --- |
| | % w/v | Range |
| Active Ingredient | 0.35 | 0.01–2% w/v |
| Polysorbate 85 | 5.0 | |
| Benzyl alcohol | 3.0 | |
| Propylene glycol | 30.0 | |
| Phosphate buffer | as pH 6.0–6.5 | |
| Water | to 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

| Veterinary oral paste | | |
| --- | --- | --- |
| | % w/w | Range |
| Active Ingredient | 4.0 | 1–20% w/w |
| Saccharin sodium | 2.5 | |
| Polysorbate 85 | 3.0 | |
| Aluminium distearate | 5.0 | |
| Fractionated coconut oil | to 100.0 | |

Disperse the aluminium distearate in the fractionated coconut oil and polysorbate 85 by heating. Cool to room temperature and disperse the saccharin sodium in the oil vehicle. Disperse the active ingredient in the base. Fill into plastic syringes.

| Granules for veterinary in-feed administration | | |
| --- | --- | --- |
| | % w/w | Range |
| Active Ingredient | 2.5 | 0.05–5% w/w |
| Calcium sulphate, hemi-hydrate | to 100.0 | |

Blend the Active Ingredient with the calcium sulphate Prepare the granules using a wet granulation process. Dry using a tray or fluid-bed drier. Fill into the appropriate container.

| Veterinary Pour-on | | |
| --- | --- | --- |
| | % w/v | Range |
| Active Ingredient | 2.0 | 0.1 to 30% |
| Dimethyl sulphoxide | 10.0 | |
| Methyl Isobutyl ketone | 30.0 | |
| Propylene glycol (and pigment) | to 100.0 | |

Dissolve the active ingredient in the dimethyl sulphoxide and the methyl isobutyl ketone. Add the pigment and make up to volume with the propylene glycol. Fill into the pour-on container.

| Emulsifiable Concentrate | |
| --- | --- |
| Active ingredient | 50 g |
| Anionic emulsifier (e.g. Phenyl sulphonate CALX) | 40 g |
| Non-ionic emulsifier (e.g. Synperonic NP13)* | 60 g |
| Aromatic solvent (e.g. Solvesso 100) to 1 liter. | |

*Trademark of ICI

Mix all ingredients, stir until dissolved.

| Granules | |
| --- | --- |
| (a) Active ingredient | 50 g |
| Wood resin | 40 g |
| Gypsum granules (20–60 mesh) (e.g. Agsorb 100A) | to 1 kg |
| (b) Active ingredient | 50 g |
| Synperonic NP13* | 40 g |
| Gypsum granules (20–60 mesh) | to 1 kg |

*Trademark of ICI

Dissolve all ingredients in a volatile solvent e.g. methylene chloride, add to granules tumbling in mixer. Dry to remove solvent.

We claim:

1. Compounds of formula (1)

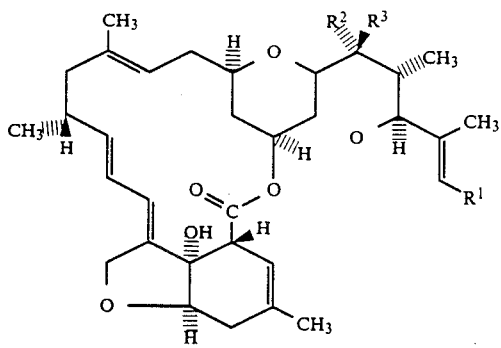

and salts thereof wherein $R^1$ is amethyl, ethyl or isopropyl group;

$R^2$ represents a group $OR^4$ where $R^4$ is of the formula $CO_2R^6$ or $CSOR^6$ where $R^6$ is a $C_1$-$C_4$ alkyl, a $C_1$-$C_4$ alkenyl, a $C_1$-$C_4$ alkynyl, a $C_3$-$C_{12}$ cycloalkyl, an aralkyl or an aryl group, a formyloxyl group, a group $R^7$ where $R^7$ is as defined above for $R^6$, a group $SO_2R^8$ where $R^8$ is as a $C_{1-4}$ alkyl or $C_{6-10}$ aryl group, a silyloxy group, a cyclic or acyclic acetaloxy group, a group $CO(CH_2)_nCO_2R^9$ where $R^9$ is a hydrogen atom or a group as defined for $R^6$ and n represents zero, 1 or 2 or a group $R^{10}R^{11}NCO_2$ where $R^{10}$ and $R^{11}$ may each independently represent a hydrogen atom or a $C_{1-4}$ alkyl group, and $R^3$ represents a hydrogen atom, or $R^2$ and $R^3$ together with the carbon atom to which they are attached represent $>C=CH_2$, $>C=O$ or $>C=NOR^5$ where $R^5$ is a hydrogen atom or a $C_{1-8}$ alkyl group and the group $>C=NOR^5$ is in the E configuration.

2. Compounds according to claim 1 in which $R^1$ is an isopropyl group.

3. Compounds according to claim 1 in which $R^2$ is an ethoxy group and $R^3$ is a hydrogen atom, or in which $R^2$ and $R^3$ together represent $=CH_2$, $=O$ or $=NOR^5$.

4. Compounds according to claim 1 in which $R^2$ and $R^3$ together represent $=NOCH_3$.

5. Compounds according to claim 1 in which $R^1$ is an isopropyl group $R^2$ is an ethoxy group and $R^3$ is a hydrogen atom, or in which $R^2$ and $R^3$ together represent $=CH_2$, $=O$ or $=NOCH_3$.

6. A composition for use in human and veterinary medicine comprising 1 to 2,000 μg/kg bodyweight of at least one compound according to claim 1 together with one or more carriers and/or excipients.

7. A pest control composition containing an effective amount of at least one compound according to claim 1 together with one or more carriers and/or excipients.

8. A method for combatting pests in agriculture, horticulture or forestry, or in stores, buildings or other public places or locations of the pests, which comprises applying to plants or other vegetation or to the pests themselves or a loation thereof an effective amount of one or mroe compounds according to claim 1.

9. A method as claimed in claim 8 in which said pests are insect, acarine or nematode pests.

* * * * *